United States Patent [19]

Hornback et al.

[11] Patent Number: 5,272,265
[45] Date of Patent: Dec. 21, 1993

[54] 3-(SUBSTITUTED OR UNSUBSTITUTED) THIAZOLO-1-CARBA (1-DETHIA)CEPHEMS

[75] Inventors: William J. Hornback; John E. Munroe, both of Indianapolis, Ind.

[73] Assignee: Eli Lilly and Company, Indianapolis, Ind.

[21] Appl. No.: 918,195

[22] Filed: Jul. 22, 1992

Related U.S. Application Data

[60] Division of Ser. No. 543,251, Jun. 25, 1990, Pat. No. 5,179,088, which is a continuation-in-part of Ser. No. 478,310, Feb. 12, 1990, abandoned.

[51] Int. Cl.$^5$ .................. C07D 487/04; A61K 31/435
[52] U.S. Cl. ...................................... 540/205; 514/210
[58] Field of Search .......................................... 540/205

[56] References Cited

U.S. PATENT DOCUMENTS

| | | | |
|---|---|---|---|
| 5,077,287 | 12/1991 | Ternansky | 540/205 |
| 5,089,610 | 2/1992 | Ternansky | 540/205 |
| 5,179,088 | 1/1993 | Hornback et al. | 514/210 |

FOREIGN PATENT DOCUMENTS

| | | |
|---|---|---|
| 0327239 | 8/1989 | European Pat. Off. . |
| 2531710 | 2/1984 | France . |
| 59-139381 | 10/1984 | Japan . |

OTHER PUBLICATIONS

R. A. Firestone et al., *J. of Medicinal Chemistry*, 1977, vol. 20, No. 4, pp. 551-556.

Guthikonda et al., *J. Am. Chem. Soc.*, 96, No. 24, pp. 7584-7585 (1974).

J. F. Peyronel et al., "Recent Advances in the Chemistry of β-lactam Antibiotics", Royal Society of Chemistry, London, 1985; Publ. No. 52, p. 336.

*Primary Examiner*—Nicholas S. Rizzo
*Attorney, Agent, or Firm*—James J. Sales; Leroy Whitaker

[57] ABSTRACT

1-Carba(1-dethia)cephem antibacterial agents possessing a 3-(substituted or unsubstituted)thiazolo group are provided. Further provided is a method for treating bacterial infections in man and other animals and a pharmaceutical formulation utilizing said 1-carba(1-dethia)cephems.

1 Claim, No Drawings

3-(SUBSTITUTED OR UNSUBSTITUTED) THIAZOLO-1-CARBA (1-DETHIA)CEPHEMS

This application is division of application Ser. No. 07/543,251, filed Jun. 25, 1990, now U.S. Pat. No. 5,179,088, which is a continuation-in-part of application Ser. No. 07/478,310, filed Feb. 12, 1990, abandoned.

BACKGROUND OF THE INVENTION

In the field of antibacterial therapy, the need for new chemotherapeutic agents is one that will never extinguish. Mutant strains resistant to existing antibacterial agents are encountered frequently. To meet this need, considerable research effort continues to focus on such new agents.

SUMMARY OF THE INVENTION

The present invention provides various 3-(substituted or unsubstituted)thiazolo-1-carba(1-dethia)-cephems (i.e., 1-carba(1-dethia)oephalosporins) useful as antibacterial agents against both gram-negative and gram-positive bacteria. The present invention provides 7$\beta$-(acylamino-1-carba(1-dethia)-3-substituted-3-cephem-4-carboxylic acids wherein the group at the 3-position is a 4-thiazole ring optionally substituted in the 2-position by nitro, cyano, phenyl, amino, halo, $C_1$-$C_6$ alkyl, $C_1$-$C_6$ substituted alkyl, an optionally-substituted heterocyclic ring, substituted phenyl, or an acyl group. Also provided are novel 7-amino intermediates useful in the preparation of the compounds of the present invention. Also provided is a pharmaceutical formulation utilizing the compounds of the present invention and a method for treating antibacterial infections in man an other animals.

DETAILED DESCRIPTION OF THE INVENTION

The present invention provides compounds of Formula (1):

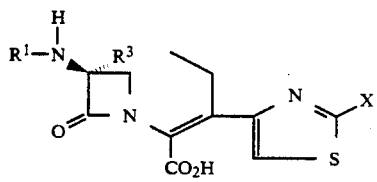

wherein X is a group selected from amino, halo, cyano, hydrogen, nitro, $C_1$-$C_6$ alkyl, $C_1$-$C_6$ substituted alkyl, a $C_3$ to $C_6$ heterocylic ring containing 1, 2, or 3 nitrogen atoms and 0 or 1 sulfur or oxygen atoms, said ring optionally substituted by one or more groups selected from halo, nitro, hydroxy, $C_1$-$C_6$ alkyl, or $C_1$-$C_6$ substituted alkyl; phenyl, substituted phenyl or an acyl group of the formula

wherein $R^{11}$ is $C_1$-$C_6$ alkyl, $C_1$-$C_6$ substituted alkyl, phenyl, or substituted phenyl; $R^3$ is hydrogen, $C_1$-$C_4$ alkoxy, or a group of the formula —NHCHO; and $R^1$ is an acyl group of the formula

wherein $R^2$ is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, or trifluoromethylthio; a phenyl or substituted phenyl group represented by the formula

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, mono- or di($C_1$-$C_4$ alkyl)amino, $C_1$-$C_4$ alkanoylamino, $C_1$-$C_4$ alkylsulfonylamino, carboxy, carbamoyl, hydroxymethyl, aminomethyl, or carboxymethyl;

a group represented by the formula

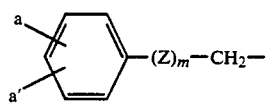

wherein a and a' have the same meanings as defined above, Z is O or S, and m is 0 or 1;

a heteroarylmethyl group represented by the formula

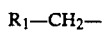

wherein $R_1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino;

a substituted methyl group represented by the formula

wherein $R_2$ is cyclohex-1,4-dienyl, or a phenyl group or substituted phenyl group represented by the formula

wherein a and a' have the above defined meanings, or $R_2$ is $R_1$ as defined above, and Q is hydroxy, $C_1$-$C_4$ alkanoyloxy, carboxy, sulfo, or amino;

or $R^2$ is a keto group or an oximino-substituted group represented by the formulae

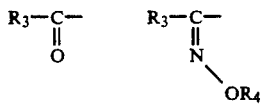

wherein $R_3$ is $R_1$ or $R_2$ as defined above and $R_4$ is hydrogen, $C_1$-$C_4$ alkyl, or a group represented by the formula

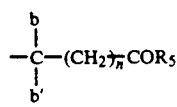

wherein b and b' independently are hydrogen, or $C_1$-$C_3$ alkyl, and b and b' when taken together with the carbon to which they are bonded form a 3- to 6-membered carbocyclic ring, $R_5$ is hydroxy, $C_1$-$C_4$ alkoxy, amino, $C_1$-$C_4$ alkylamino, or di($C_1$-$C_4$ alkyl)amino, and n is 0, 1, 2, or 3;
or a pharmaceutically acceptable salt thereof.

In the above Formula (1), one preferred $R_2$ group is a keto group or an oximino-substituted group represented by the formulae

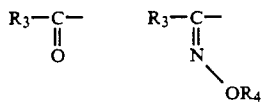

wherein $R_3$ is $R_1$ or $R_2$ as defined above and $R_4$ is hydrogen, $C_1$-$C_4$ alkyl, or a group represented by the formula

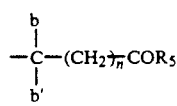

wherein b and b' independently are hydrogen, or $C_1$-$C_3$ alkyl, and b and b' when taken together with the carbon to which they are bonded form a 3- to 6-membered carbocyclic ring, $R_5$ is hydroxy, $C_1$-$C_4$ alkoxy, amino, $C_1$-$C_4$ alkylamino, or di($C_1$-$C_4$ alkyl)amino, and n is 0 1, 2, or 3.

A preferred $R^1$ group is (2-aminothiazol-4-yl)methoximinoacetyl.

A further preferred $R^2$ group is a substituted methyl group represented by the formula

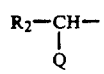

wherein $R_2$ is cyclohex-1,4-dienyl, or a phenyl group or substituted phenyl group represented by the formula

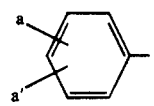

wherein a and a' have the above defined meanings, or $R_2$ is $R_1$ as defined above, and Q is hydroxy, $C_1$-$C_4$ alkanoyloxy, carboxy, sulfo, or amino.

A preferred $R^1$ group is D-phenylglycyl.

As a further aspect of the present invention, there are provided intermediates of Formula (2)

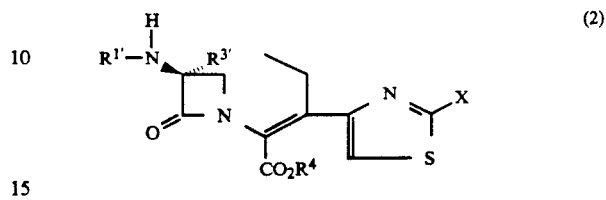

wherein: $R^{1'}$ is hydrogen or an amino protecting group; $R^4$ is hydrogen or a carboxy protecting group; $R^{3'}$ is hydrogen, $C_1$-$C_4$ alkoxy, or a group of the formula —NHCHO; and X is a group selected from amino, halo, cyano, hydrogen, nitro, $C_1$-$C_6$ alkyl, $C_1$-$C_6$ substituted alkyl, a $C_3$ to $C_6$ heterocylic ring containing 1, 2, or 3 nitrogens and 0 or 1 sulfur or oxygen atoms, said ring optionally substituted by one or more groups selected from halo, nitro, hydroxy, $C_1$-$C_6$ alkyl, or $C_1$-$C_6$ substituted alkyl; phenyl, substituted phenyl, or an acyl group of the formula

wherein $R'''$ is $C_1$-$C_6$ alkyl, $C_1$-$C_6$ substituted alkyl, phenyl, or substituted phenyl. The compounds of formula (2) are useful as intermediates to the antibacterial agents of formula (1)

In the above Formula (1), the term "$C_1$ to $C_6$ alkyl" denotes such radicals as methyl, ethyl, n-propyl, isopropyl, n-butyl, sec-butyl, tert-butyl, amyl, tertamyl, hexyl and the like. The preferred "$C_1$ to $C_6$ alkyl" group is methyl.

The term "$C_1$ to $C_6$ substituted alkyl" denotes the above $C_1$ to $C_6$ alkyl groups that are substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino, $C_1$ to $C_4$ alkoxy, phenyl, substituted phenyl, or a $C_3$ to $C_6$ heterocyclic ring containing 1, 2, or 3 nitrogen atoms and 0 or 1 sulfur or oxygen atoms, said ring optionally substituted by one or more groups selected from halo, nitro, hydroxy, or $C_1$-$C_6$ alkyl. The substituted alkyl groups may be substituted once or twice with the same or with different substituents.

Examples of the above substituted alkyl groups include cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxy methyl, acetoxymethyl, chloromethyl, bromomethyl, iodomethyl, 6-hydroxyhexyl, 2,4-dichloro(n-butyl), 2-amino(iso-propyl), 2-carbamoyloxyethyl chloroethyl, bromoethyl, fluoroethyl, iodoethyl, chloropropyl, bromopropyl, fluoropropyl, iodopropyl, phenylmethyl, phenylethyl, phenyl (3-pyridyl)methyl, phenyl(3-pyridyl)ethyl, and the like.

The term "$C_1$ to $C_4$ alkoxy" as used herein denotes groups such as methoxy, ethoxy, n-propoxy, isopropoxy, n-butoxy, t-butoxy and like groups.

The term "substituted phenyl" as used herein denotes a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, amino, protected amino, aminomethyl, protected aminomethyl, trifluoromethyl or N-(methylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(iso-propoxy)phenyl, 4-(t-butoxy)phenyl, 3-ethoxy-4-methoxyphenyl and the like; 3- or 4- trifluoromethylphenyl; a mono- or dicarboxyphenyl or (protected carboxy)phenyl group such as 4-carboxyphenyl or 2,4-di(-protected carboxy)phenyl; a mono- or di-(hydroxymethyl)phenyl or (protected hydroxymethyl)-phenyl such as 3-(protected hydroxymethyl-)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)-phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The terms "halo" and "halogen" refer to the fluoro, chloro, bromo or iodo groups.

The term "pharmaceutically-acceptable salt" encompasses those salts that form with the carboxylate anions and includes salts formed with the organic and inorganic cations discussed above. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "carboxy-protecting group" as used herein refers to one of the ester derivatives of the carboxylic acid group commonly employed to block or protect the carboxylic acid group while reactions are carried out on other functional groups on the compound Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4'-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) A preferred carboxylic acid protecting group is the allyl group. Similar carboxy-protecting groups used in the cephalosporin, penicillin and peptide arts can also be used to protect a carboxy group substituents. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

The term "amino-protecting group" as used herein refers to substituents of the amino group commonly employed to block or protect the amino functionality while reacting other functional groups on the compound. Examples of such amino-protecting groups include the formyl group, the trityl group, the t-butoxycarbonyl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of aminoprotecting group employed is not critical so long as the derivatized amino group is stable to the condition of subsequent reaction(s) on other positions of the molecule and can be removed at the appropriate point without disrupting the remainder of the molecule. Preferred amino-protecting groups are the allyloxycarbonyl, the t-butoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In Formulae (1) and (2) above, when X is a $C_3$-$C_6$ heterocyclic ring containing 1, 2, or 3 nitrogen atoms and 0 or 1 sulfur or oxygen atoms, (i.e., a heterocyclic ring containing from 3 to 6 carbon atoms, 1, 2, or 3 nitrogen atoms and 0 or 1 sulfur or oxygen atoms) said ring optionally substituted by one or more halo, nitro, hydroxy, $C_1$-$C_6$ alkyl, or $C_1$-$C_6$ substituted alkyl groups, examples of such rings include pyrrolyl, furanyl, 4-nitrothiazol-2-yl, imidazolyl, pyridinyl, pyrimidinyl, pyrazinyl, morpholinyl, oxazolyl, thiazolyl, thiadiazolyl, oxadiazolyl, 1-methyl-3-pyridyl, 2-methyl-3-pyridyl, 3-methyl-4-nitro-imidazol-2-yl, and the like.

One intermediate (VI) can be prepared according to the following Scheme (A)

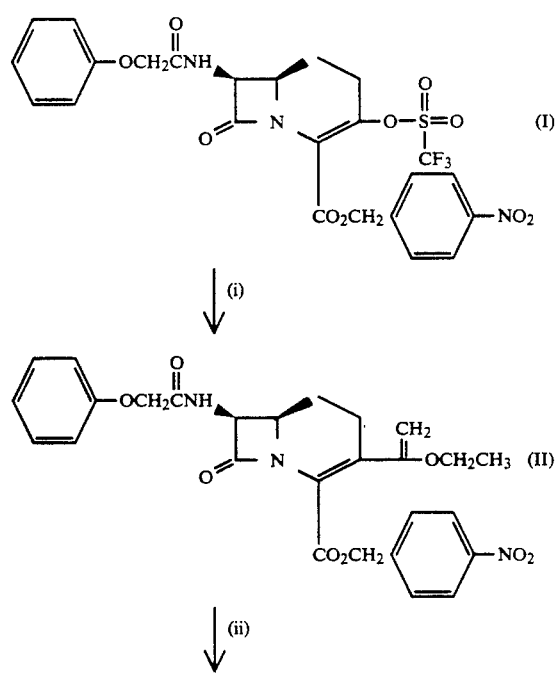

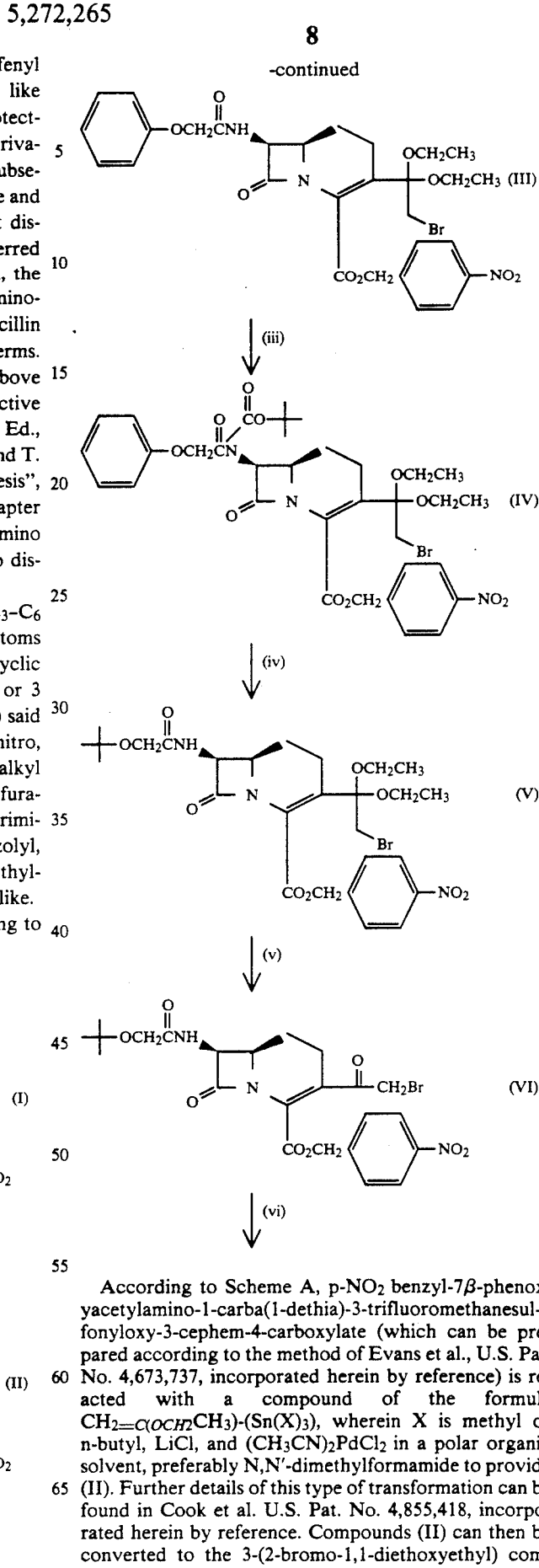

According to Scheme A, p-$NO_2$ benzyl-7$\beta$-phenoxyacetylamino-1-carba(1-dethia)-3-trifluoromethanesulfonyloxy-3-cephem-4-carboxylate (which can be prepared according to the method of Evans et al., U.S. Pat. No. 4,673,737, incorporated herein by reference) is reacted with a compound of the formula $CH_2=C(OCH_2CH_3)$-$(Sn(X)_3)$, wherein X is methyl or n-butyl, LiCl, and $(CH_3CN)_2PdCl_2$ in a polar organic solvent, preferably N,N'-dimethylformamide to provide (II). Further details of this type of transformation can be found in Cook et al. U.S. Pat. No. 4,855,418, incorporated herein by reference. Compounds (II) can then be converted to the 3-(2-bromo-1,1-diethoxyethyl) compound (III) with $Br_2/CCl_4$ in ethanol/$CH_2Cl_2$ using a base such as 2,6-lutidine.

Reactions (iii) and (iv) depict a method whereby the 7-phenoxyacetyl group may be replaced by the t-butoxycarbonyl group. First, compound (III) is acylated with di-tert-butoxydicarbonate in the presence of a base such as dimethylaminopyridine.

Secondly, the phenoxyacetyl group is displaced with a base such as LiOH in a polar solvent such as tetrahydrofuran. Further description of this exchange can be found in Blaszczak et al., European Patent Application No. 88306996.5.

Finally, the 3-bromomethylcarbonyl compound (VI) can then be prepared from compound V by an acid catalyzed hydrolysis reaction with, for example, acetic acid in acetonitrile/water.

Compounds of Formula (1) can then be made from intermediate (VI) above by the following Scheme (B):

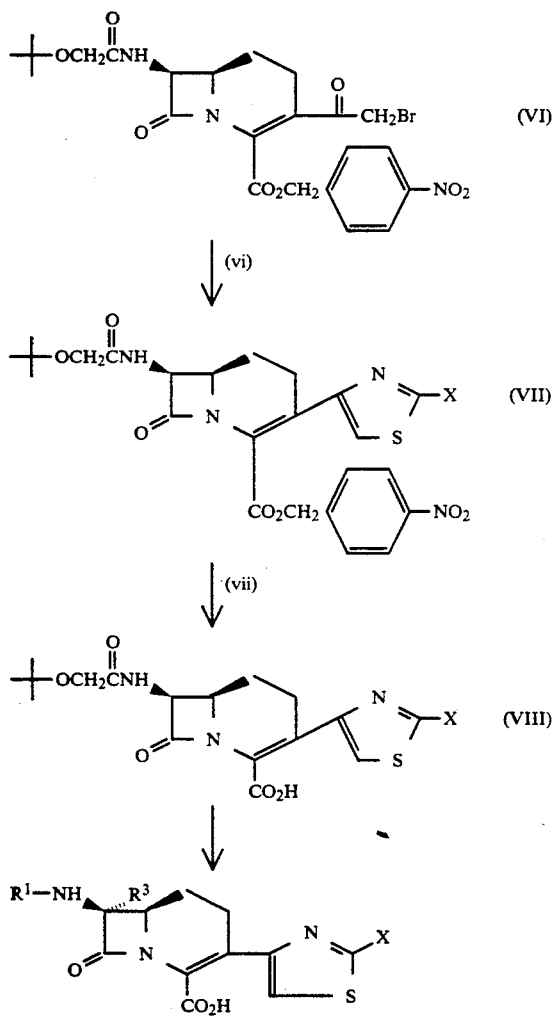

In the above step (vi), the 3-(2-substituted) thiazolo compounds may be synthesized by reaction of intermediate (VI) with a compound of the formula

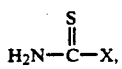

wherein X is as defined in Formula 1, above. Thus, with the desired 3-(2-substituted thiazol-4-yl) substituent in place, and with the de-esterification of the 4-p-nitrobenzyl ester occasionally occurring under the previously defined reaction conditions, the 4-carboxy position may be re-esterified to the 4-allyl ester using allyl bromide, NaI, $(CH_3CH_2CH_2CH_2)_4NHSO_4$, and $NaHCO_3$ in N,N'-dimethylformamide. If deesterification does not occur under these conditions, the p-nitrobenzyl protecting group may be removed by zinc reduction in a solvent mixture of N,N'-dimethylformamide/tetrahydrofuran/acetic acid or N,N'-dimethylformamide/tetrahydrofuran in HCl and reesterified as described above to the 4-allyl ester. The resulting amino protected, carboxy protected "nucleus" (i.e., formula (2)) can then be treated with p-toluenesulfonic acid·$H_2O$ or trifluoroacetic acid to remove the 7-t-butoxycarbonyl group to provide the 7-amino 4-carboxy protected intermediate. Further, the 7-amino group can then be acylated with an activated form of the desired $R^1$ substituent using standard procedures well-known in the β-lactam art. Finally, all remaining amino and/or carboxy protecting groups can then be removed using conventional methodology.

The 7β-acylamino-7α-substituted-1-carbacephalosporins represented by Formula (1) wherein $R^3$ is $C_1$–$C_4$ alkoxy can be prepared according to the method described by Koppel, U.S. Pat. No. 3,994,885, incorporated herein by reference.

The 7α-formamido substituted compounds wherein $R^3$ is —NHCHO can be obtained by the method described by Millner, U.S. Pat. No. 4,539,159 incorporated herein by reference. According to this method, a 7β-acylamino- or 7β-protected amino-7α-methylthio-substituted 1-carbacephalosporin is reacted with anhydrous ammonia or an ammonium salt in the presence of mercuric acetate to form the corresponding 7α-amino derivative. The latter is formylated to the 7α-formamido derivative.

One skilled in the art will appreciate that although the above manipulations utilized phenoxyacetyl and t-butyloxycarbonyl as amino protecting groups and the p-nitrobenzyl group as carboxy-protecting group, there are many which would be equally efficacious.

The 1-carbacephalosporins provided by the invention form salts with suitable bases, in particular, the pharmaceutically-acceptable, non-toxic salts. The C-4 carboxy group of the 1-carbacephalosporin can form salts with the alkali and alkaline earth metal hydroxides, carbonates and bicarbonates. Examples of such pharmaceutically-acceptable salts are the sodium, potassium, calcium and magnesium salts. Salts also may be formed with amines such as dibenzylamine, cyclohexylamine, triethylamine, ethanolamine, di-ethanolamine and like amines. Likewise, when the 1-carbacephalosporin is substituted by two or more carboxy groups, di- and tri-salts are obtained by conventional salt-forming methods.

The pharmaceutically-acceptable, non-toxic salts can be useful forms of the antibiotics for preparing antibiotic formulations.

This invention also provides a method for treating infectious diseases in man and other animals caused by bacteria and pharmaceutical formulations suitable for administration in the treatment method. The therapeutic method of this invention comprises administering to man or other animals an antibiotically effective non-toxic dose of a compound represented by Formula (1) or a pharmaceutically acceptable salt thereof.

An antibiotically effective amount is an amount between about 25 mg and about 2 grams. The compound or salt may be administered in a single dose or in multiple doses throughout the day. Treatment may continue for a week to ten days or longer depending upon the duration of the infection. The particular dose and regimen can depend on such factors as the weight and age of the patient, the particular causative organism, the severity of the infection, the general health of the patient, and the tolerance of the individual to the antibiotic.

The 1-carbacephalosporins may be administered parenterally, orally, subcutaneously or rectally. As with other β-lactam antibiotics, the method of this invention may be used prophylactically to prevent infections after exposure or before possible exposure, e.g., preoperatively The antibiotic 1-carbacephalosporins may be administered by conventional methods, e.g., in capsules, tablets, by syringe, or by intravenous drip.

The pharmaceutical formulations of the invention comprise an antibiotically effective non-toxic amount of a 1-carbacephalosporin represented by Formula (1) or a pharmaceutically acceptable salt thereof, and a pharmaceutically acceptable carrier.

Formulations for oral administration include capsules, tablets, lozenges and liquid suspensions. The antibiotic or a salt thereof in the form of a dry powder can be encapsulated in gelatin capsules for oral use. The antibiotic may also be blended with an excipient, e.g., a stabilizer, prior to filling. Capsules may contain between about 100 mg and about 500 mg to provide unit dosage formulations.

Tablets containing between about 100 mg and 500 mg of the antibiotic or a pharmaceutically acceptable salt thereof can be formulated by conventional means and may contain in addition a binding agent, disintegrating agent, stabilizing agent, antioxidant, etc.

Liquid preparations of the antibiotic may be prepared for infant and geriatric use. Pediatric suspensions can be formulated with the antibiotic oral excipients such as suspending agents, flavoring agents, stabilizers and the like. Solutions of the antibiotics likewise may be formulated with solubilizing agents, flavoring agents, sugar, water, etc.

Parenteral formulations of the antibiotics for injection are formulated with Water-for-Injection, Ringer's solution, physiological saline or glucose solution. The antibiotic also may be administered in an intravenous fluid by the drip method.

For parenteral use, the antibiotic or a pharmaceutically acceptable salt thereof, can be made up preferably in dry crystalline powder form or as a lyophilized powder and filled into vials. Such vials may contain between about 100 mg and about 2 grams of antibiotic per vial.

The following Experimental Section provides further examples of the various aspects of the present invention but is not to be construed as limiting the scope therefor.

Experimental Section

Preparation 1 p-Nitrobenzyl 7β-phenoxyacetylamido-1-carba(1-dethia)-3-trifluoromethanesulfonyloxy-3-cephem-4-carboxylate The title compound can be prepared according to the method of Evans and Sjogren, U.S. Pat. No. 4,673,737, incorporated herein by reference.

Preparation 2

Trimethyl(1-ethoxy-ethen-1-yl)stannane (Ref: Organometallics, Vol. 1, No. 6, 1982, J. Soderquist)

A 19.18 ml (14.48 g, 200.36 mmol) sample of ethoxyethylene was dissolved in 100 ml of tetrahydrofuran, cooled to $-78°$ C., and treated with a solution of t-butyllithium (94.1 ml, 150.56 mmol, 1.6M) over 20 min. under argon. The reaction mixture was then allowed to warm to $0°$ C. over 35 min. and added via cannula to a $-78°$ C. solution of 20.0 g (100.4 mmol) of chlorotrimethylstannane in 40 ml of tetrahydrofuran and allowed to warm to room temperature gradually. After an additional 50 min., the mixture was quenched with saturated $NH_4Cl$ solution (400 ml) and extracted with diethyl ether (500 ml) The ether solution was then dried over anhydrous $Na_2SO_4$, filtered and concentrated to provide the crude product as a yellowish liquid (23.8 g; 100%). The crude product was then distilled at $40°-41°$ C. and about 4 mm Hg to provide 12.05 g of the title compound.

$^1$H NMR (300 MHz, $CDCl_3$) δ4.65 (s, 1H), 4.10 (s, 1H), 3.70 (q, 2H), 1.25 (t, 3H), and 0.18 (s, 9H).

Preparation 3 p-Nitrobenzyl 7β-phenoxyacetylamino-1-carba(1-dethia)-3-(1-ethoxy-ethen-1-yl)-3-cephem-4-carboxylate.

A 1.0 g (1.77 mmol) sample of the title compound of Preparation 1, a 0.142 g (3.34 mmol) sample of lithium chloride, and a 0.043 g (0.167 mmol) sample of dichloropalladium (II) diacetonitrilate were dissolved in 3 ml of dimethylformamide and treated with 0.435 g (1.84 mmol) of trimethyl (1-ethoxy-ethen-1-yl)stannane. The reaction was then gently warmed with a hot air gun for about 10 seconds, and allowed to stir at room temperature for about one hour. The reaction mixture was poured into 100 ml 1:1 mixture of ethyl acetate/diethyl ether and 100 ml 10:1 mixture Brine/satd. $NaHCO_3$ solution. Organics were separated and dried over $Na_2SO_4$, filtered, and concentrated in vacuo. Resultant crude dark oil was then diluted with 2 ml $CH_2Cl_2$ and 5 ml diethyl ether and 20 ml of hexane. A dark oil again resulted. Supernatant was decanted and to it was added an additional 40 ml hexane. Desired precipitated as a solid which was filtered and washed with hexane and dried to give 87 mg of the desired compound. The dark oil was chromatographed on 50 g of silica gel using 15%-25% ethyl acetate/$CH_2Cl_2$ as eluent. The resulting product fractions were concentrated in vacuo and treated with 20 ml $Et_2O$ to provide 550 mg of the title compound (total yield 637 mg, 74%).

$^1$H NMR (300 MHz, $CDCl_3$) δ8.20 (d, J=9Hz, 2H), 7.60 (d, J=9Hz, 2H), 7.35 (t, J=8Hz, 2H), 7.10 (m, 2H), 6.90 (d, J=8Hz, 2H), 5.45 (dd, J=5,7Hz, 1H), 5.37 (AB, 2H), 58 (S, 2H), 4.21 (d, J=3 Hz, 1H), 4.18 (d, J=3Hz, 1H), 3.95 (m, 1H), 3.7S (m, 2H), 2.70 (dd, J=4, 18Hz, 1H), 2.30 (m, 1H), 2.05 (m, 1H), 1.50 (m, 1H) and 1.2S (t, J=7Hz, 3H)

IR: ($CHCl_3$) 3028, 1772, 1734, 1691, 1524, 1496, 1389, 1299, 1277, and 1207 $cm^{-1}$ MS: m/e 521 (M+)

Analysis Calculated for $C_{27}H_{27}N_3O_8$:
Calc.: C, 62.18; H, 5.22; N, 8.06;
Found: C, 62.43; H, 5.36; N, 8.30.

Preparation 4 p-Nitrobenzyl 7β-phenoxyacetylamino-1-carba(1-dethia)-3-(2-bromo-1,1-diethoxyethyl)-3-cephem-4-carboxylate A 570 mg sample of the material from Preparation 4 was dissolved in 4.5 ml of ethanol/2 ml of CH$_2$Cl$_2$ and cooled to 0° C. The solution was then treated with 0.153 ml (1.312 mmol) of 2,6-lutidine and 1.1 ml (1.1 mmol) of a 1.0 M Br$_2$/CCl$_4$ solution. The resulting mixture was then poured into a mixture of saturated sodium bicarbonate solution and 1:1 ethyl acetate/diethyl ether. The organic layer was separated, dried over anhydrous Na$_2$SO$_4$, filtered, and concentrated to provide a yellow foam which was used directly in the next step.

A 25 mg sample of the above product was purified over a silica gel (2.5 g) column using 7% ethyl acetate/CH$_2$Cl$_2$ as eluent to provide 20 mg of the title compound.

$^1$H NMR (300 MHz, CDCl$_3$) δ8.23 (d, J=9Hz, 2H), 7.60 (d, J=9Hz, 2H) 7.35 (t, J=8Hz, 2H), 7.10 (m, 2H), 6.95 (d, J=8Hz, 2H), 5.35 (AB, 2H) 5.32 (dd, J=5, 7Hz, 1H), 4.58 (s, 2H), 3.95 (m, 1H) 3.3–3.6 (2m, 4H), 2.48 (dd, J=2, 16Hz, 1H), 2.20 (m, 1H) 2.05 (m, 1H) 1.45 (m, 1H) 1.16 (t, J=4Hz, 3H) and 1.10 (t, J=4Hz, 3H)

IR (CHCl$_2$) 3019, 1772, 1751, 1749, 1695, 1349, 1290, 1206 and 1073 cm$^{-1}$

MS m/e 646 (M+ +1)

Analysis Calculated for C$_{29}$H$_{32}$N$_3$O$_9$Br:
Calc.: C, 53.88; H, 4.99; N, 6.50;
Found: C, 53.59; H, 4.75; N, 6.77.

Preparation 5 p-Nitrobenzyl 7β-phenoxyacetyl-t-butyloxycarbonylamino-1-carba(1-dethia)-3-(2-bromo-1,1-diethoxy)-3-cephem-4-carboxylate A 700 mg sample of the product of preparation was dissolved in 10 ml of CH$_2$Cl$_2$ at room temperature and treated with 0.256 ml (1.126 mmol) of di-tert-butyl dicarbonate, followed by 132 mg (1.08 mmol) of 4-dimethylaminopyridine and stirring for 30 min. An additional 50 μl of di-tert-butyl dicarbonate was added and the reaction stirred for about 30 min. The reaction mixture was chromatographed directly over a silica gel column (40 g) using 20%–30% ethyl acetate/CH$_2$Cl$_2$ as eluent to provide 730 mg (90.5%) of the title compound $^1$H NMR (300 MHz, CDCl$_3$) δ8.23 (d, J=9Hz, 2H), 7.62 (d, J=9Hz, 2H), 7.30 (t, J=8Hz, 2H), 7.0 (m, 2H), 6.95 (d, J=8Hz, 2H), 5.70 (d, J=4Hz, 1H), 5.35 (AB, 2H), 5.18 (d, J=3Hz, 2H), 3.86 (m, 1H), 3.35–3.7 (m, 4H), 2.5 (dd, J=2, 18Hz, 1H), 2.18 (m, 1H), 1.85 (m, 1H) 1.55 (s, 9H) 1.50 (m, 1H) 1.16 (t, J=4Hz, 3H) and 1.10 (t, J=4Hz, 3H)

IR: (CHCl$_3$) 3019, 1791, 1747, 1349, 1226, 1205, and 1145 cm$^{-1}$

MS: m/e 672 (M+ —OC$_4$H$_9$)

Analysis Calculated for C$_{34}$H$_{40}$N$_3$O$_{11}$Br:
Calc.: C, 54.70; H, 5.40; N, 5.63;
Found: C, 53.55; H, 4.48; N, 6.42.

Preparation 6 p-Nitrobenzyl 7β-t-butyloxycarbonylamino-1-carba(1-dethia)-3-(2-bromo-1,1-diethoxyethyl-3-cephem-4-carboxylate A 750 mg (0.957 mmol) sample of the product of Preparation 5 was dissolved in 8 ml of tetrahydrofuran, treated with 0.85 ml (0.85 mmol) of 1.0 M lithium hydroxide soln. and sonicated. A further 0.155 ml portion of lithium hydroxide was added and sonication continued for 30 min. The reaction mixture was then poured into 50 ml of saturated sodium bicarbonate/75 ml ethyl acetate solution. The organic phase was separated and dried over anhydrous Na$_2$SO$_4$, filtered, and concentrated to provide 410 mg of the product as a foam after column chromatography over silica gel (8% ethyl acetate/CH$_2$Cl$_2$).

The above chromatography provided 176 mg of starting material which was re-submitted to the above conditions to obtain 102 mg of the title compound. Total yield=512 mg (86.6%).

$^1$H NMR: (300 MHz, CDCl$_3$) δ8.23 (d, J=9Hz, 2H), 7.61 (d, J=9Hz, 2H), 5.35 (AB, 2H), 5.01 (m, 1H), 5.09 (m, 1H), 3.85 (m, 1H), 3.3–3.6 (m, 4H), 2.47 (dd, J=2, 16Hz, 1H), 2.20 (m, 1H), 2.10 (m, 1H), 1.43 (s, 9H), 1.12 (t, J=4Hz, 3H), and 1.08 (t, J=4Hz, 3H)

IR: (CHCl$_3$) 1769, 1741, 1716, 1524, 1349, 1224, 1207, and 1160 cm$^{-1}$

MS: 611 (M+)

Analysis Calculated for C$_{26}$H$_{34}$N$_3$O$_9$Br:
Calc.: C, 50.99; H, 5.60; N, 6.86;
Found: C, 51.99; H, 5.16; N, 7.67.

Preparation 7 p-Nitrobenzyl 7β-t-butoxycarbonylamino-1-carba(1-dethia)-3-(2-bromomethylcarbonyl)-3-cephem-4-carboxylate A 125 mg (0.204 mmol) sample of the product 0 25 ml of acetic acid/0.05 ml H$_2$O and stirred for about 2 hours. The reaction mixture was then poured into (50 ml) saturated sodium bicarbonate solution/(100 ml) 1:1 ethyl acetate/diethyl ether solution. The organic phase was separated, dried over anhydrous Na$_2$SO$_4$, filtered, and concentrated to provide 111 mg (about 100%) of the title compound as a white solid.

$^1$H NMR: (300 MHz, CDCl$_3$) δ8.20 (d, J=9Hz, 2H), 7.62 (d, J=9Hz, 2H), 5.33 (AB, 2H), 5.28 (dd, J=4,7Hz, 1H), 5.25 (d, J=4Hz, 1H), 4.03 (AB, 2H), 3.87 (m, 1H), 2.80 (dd, J=4,18Hz, 1H), 2.45 (m, 1H), 2.13 (m, 1H) 1.57 (m, 1H), and 1.4 (s, 9H)

IR: (CHCl$_3$) 3019, 1782, 1718, 1525, 1369, 1291, and 1159 cm$^{-1}$

MS: m/e 480 (M+ —C$_4$H$_9$)

Analysis Calculated for C$_{22}$H$_{24}$N$_3$O$_8$Br:
Calc.: C, 49.08; H, 4.49; N, 7.81;
Found: C, 49.29; H, 4.64; N, 7.62.

Example 1

7β-t-butoxycarbonylamino-1-carba(1-dethia)-3-(2-phenylthiazolo)-3-cephem-4-carboxylic acid A 75 mg (0.140 mmol) sample of p-nitrobenzyl 7β-t-butoxycarbonylamino-1-carba(1-dethia)-3-bromomethylcarbonyl)-3-cephem-4-carboxylate (Preparation 7) was dissolved in 1.5 ml of isopropanol and 1 ml of 1,1,2-trichloroethane, followed by the addition of 20 mg (0.146 mmol) of phenylthiocarbamate. The reaction mixture was then heated to about 65° C. for 1.5 hours. The reaction mixture was concentrated in vacuo and treated with 3 ml of diethyl ether/4 ml hexane. The resulting solid (85% yield) was dried to provide the title compound.

Example 2

7β-t-butoxycarbonylamino-1-carba(1-dethia)-3-(2-(4-NO$_2$-3-methylimidazol-2-yl)-thiazol-4-yl-3-cephem-4-carboxylic acid A 127 mg sample of p-nitrobenzyl 7β-t-butoxycarbonylamino-1-carba(1-dethia)-3-bromomethylcarbonyl-4-carboxylic acid was reacted with 4-NO$_2$-3-methylimidazolo thiocarbamate in a manner analogous to that of Example 1. Column chromatography ethylacetate/CH$_2$Cl$_2$ with a trace of acetic acid provided 85 mg of the title compound.

Example 3 p-Nitrobenzyl 7β-t-butoxyoarbonylamino-1-carba(1-dethia)-3-(2-(phenyl)(2-pyridyl)methylthiazol-4-yl)-3-cephem-4-carboxylate The title compound was prepared in a manner analogous to that of Example 1 (without deesterification) utilizing phenyl-2-pyridylthiocarbamate 710 mg (97.3%)

$^1$H NMR: (300 MHz, CDCl$_3$) δ8.60 (dd, J=4, 9Hz, 1H), 8.05 (d, J=9Hz, 2H), 7.60 (m, 9H), 5.83 (d, J=4Hz, 1H), 5.15 (m, 3H), 4.70 (m, 1H), 3.90 (m, 1H), 2.92 (dd, J=4, 18Hz, 1H), 2.50 (m, 1H), 2.20 (m, 1H) 1.70 (m, 1H) and 1.48 (s, 9H)

Example 4

7β-t-butoxycarbonylamino-1-carba(1-dethia)-3-(2-phenylthiazol-4-yl)-3-cephem-4-carboxylic acid A 430 mg (0.746 mmol) sample of p-nitrobenzyl 7β-t-butoxycarbonylamino-1-carba(1-dethia)-3-(2-phenylthiazol-4-yl)-3-cephem-4-carboxylate was dissolved in 5 ml dimethylformamide/6 ml tetrahydrofuran/4 ml acetic acid along with 200 mg (2.98 mmol) of Zn. Upon completion, the reaction mixture was diluted with CH$_2$Cl$_2$ and was then washed sequentially with H$_2$O, 1N HCl, and NaHCO$_3$ solution. The NaHCO$_3$ solution was layered with CH$_2$Cl$_2$, acidified to a pH of 2. The CH$_2$Cl$_2$ layer was separated and the aqueous portion extracted with CH$_2$Cl$_2$. The combined CH$_2$Cl$_2$ portions were dried over anhydrous Na$_2$SO$_4$, filtered, and concentrated. Crystallization over diethyl ether/hexane provided 270 mg (82.3%) of the title compound.

Example 5 p-Nitrobenzyl 7β-t-butoxycarbonylamino-1-carba(1-dethia)-3-(2-aminothiazol-4-yl)-3-cephem-4-carboxylate A 600 mg (1.115 mmol) sample of p-nitrobenzyl-7β-t-butoxycarbonylamino-1-carba(1-dethia)-3-(bromomethylcarbonyl)-3-cephem-4-carboxylate was dissolved in 15 ml of isopropanol/10 ml 1,1,2-trichloroethane along with 0.146 (1.25 mmol) of 2,6-lutidine followed by 88.4 mg (1.16 mmol) of thiourea.

Workup analogous to that described above provided 220 mg of the title compound.

$^1$H NMR: (300 MHz, CDCl$_3$) δ8.22 (m, 2H), 6.90 (m, 1H), 6.58 (m, 1H) 6.10 (s, 2H) 5.35 (m, 3H), 3.85 (m, 1H), 2.85 (m, 1H), 2.58 (m, 1H), 2.40 (m, 1H), 1.80 (m, 1H), and 1.45 (s, 9H)

Example 6 p-Nitrobenzyl 7β-t-butoxycarbonylamino-1-carba(1-dethia)-3-(2-(2,3-dihydroxyphenyl)thiazol-4-yl)-3-cephem-4-carboxylate In a manner analogous to preceding examples, 3,4-dihydroxyphenylthiocarbamate was utilized to provide the title compound (380 mg).

$^1$H NMR: (300 MHz, CDCl$_3$) δ7.90 (m, 2H), 7.40 (m, 1H), 7.12 (m, 3H), 6.98 (s, 1H), 6.84 (m, 1H), 5.20 (m, 4H), 4.05 (m, 1H), 2.84 (dd, J=4, 18Hz, 1H) 2.35 (m, 1H), 2.15 (m, 1H), 1.75 (m, 1H), and 1.45 (s, 9H)

Example 7 p-Nitrobenzyl 7β-t-butoxycarbonyl-1-carba(1-dethia)-3-(2-(2,3-di-(t-butyldimethylsilyloxy)phenyl)thiazol-4-yl)-3-cephem-4-carboxylate A 370 mg sample of the compound produced in Example 6 above was dissolved in 4 ml of dimethylformamide and treated with 184 mg of t-butyldimethylsilylchloride and 85 mg of imidazole and stirred for about 24 hours. An additional 180 mg of t-butyldimethylsilyl chloride and 90 mg of imidazole were added and the solution stirred an additional 24 hours.

The reaction mixture was then diluted with 100 ml of ethyl acetate and 100 ml of H$_2$O. The organic phase was separated and washed with 100 ml of saturated NaHCO$_3$ solution. The organic phase was then dried over anhydrous Na$_2$SO$_4$ and purified over (50 g) silica gel using ethyl acetate as eluent. Further chromatography over silica gel (25% ethyl acetate/hexane) provided 320 mg of p-nitrobenzyl 7β-t-butoxycarbonylamino-1-carba(1-dethia)-3-(3,4-di(t-butyldimethylsilyloxy)phenyl-thiazol-4-yl-3-cephem-4-carboxylate.

$^1$H NMR: (300 MHz, CDCl$_3$) δ8.0 (d, J=9Hz, 2H), 7.32 (m, 2H), 7.22 (d, J=9Hz, 2H), 7.05 (s, 1H), 6.80 (m, 1H), 5.28 (AB, 2H), 5.22 (m, 1H), 5.05 (m, 1H), 3.95 (m, 1H), 2.95 (dd J=4, 18Hz, 1H), 2.55 (m, 1H), 2.20 (m, 1H), 1.70 (m, 1H), 1.42 (s, 9H) 1.0 (s, 9H), 0.97 (s, 9H), 0.23 (s, 6H), and 0.20 (s, 6H)

Example 8

Allyl 7β-t-butoxycarbonylamino-1-carba(1-dethia)-3-(2-(2,3-di-(t-butyldimethylsilyloxy)phenyl)-3-cephem-4-carboxylate A. Removal of p-nitrobenzyl ester A 320 mg (0.382 mmol) sample of the title compound from Example 7 was dissolved in 2.5 ml of dimethylformamide/3 ml of tetrahydrofuran and 2.5 ml of acetic acid, treated with 100 mg (1.53 mmol) of Zn dust and stirred for 20 min. The reaction mixture was then treated with an additional 1 ml of acetic acid and 100 mg of Zn. After 1 h, the reaction mixture was filtered, diluted with ethyl acetate and washed with water. The organic phase was then dried and concentrated in vacuo azeotroping any remaining dimethylformamide away with toluene (5 times) to provide the title compound as a foam (220 mg, 82%) (some desilylation occurred).

B. Formation of allyl ester

A 215 mg (0.306 mmol) sample of the product from part A above is reacted with allyl bromide in dimethylformamide in the presence of tetra-n-butylammonium hydrogen sulfate, sodium bicarbonate and sodium iodide to provide the title compound.

Example 9

Allyl 7β-t-butoxycarbonylamino-1-carba(1-dethia)-3-(2-phenylthiazol-4-yl)-3-cephem-4-carboxylate A 103 mg 0.234 mmol) sample of 7β-t-butoxycarbonylamino-1-carba(1-dethia)-3-(2-phenylthiazol-4-yl)-3-cephem-4-carboxylic acid, prepared according to the foregoing examples, was dissolved in a small amount of N,N-dimethylformamide, treated with 60 mg (0.70 mmol) of NaHCO$_3$ and stirred for 10 min. The reaction mixture was then treated with 83 mg (0.246 mmol) of tetra-n-butylammonium hydrogen sulfate, allowed to stir for 10 min., followed by treatment with 26 μl (0.294 mmol) of allyl bromide (followed by a additional 10 μl ) and 109 mg (0.725 mmol) of NaI. After stirring at room temperature overnight, the reaction mixture was poured into 30 ml of saturated NaHCO₃ solution and 50 ml of ethyl acetate. The organic phase was separated and washed (2×30 ml) with 0.5 N HCl solution, dried over anhydrous Na₂SO₄, filtered and concentrated in vacuo to provide the title compound. (100 mg, 89.3%, isolated as a solid from diethyl ether/hexane.)

¹H NMR (300 MHz, CDCl₃) δ7.90 (m, 2H), 7.40 (m, 3H), 7.15 (s, 1H), 5.78 (m, 1H), 5.10 (m, 4H), 4.65 (ABX, 2H), 3.90 (m, 1H), 2.95 (dd, J=4, 18Hz, 1H), 2.50 (m, 1H), 2.20 (m, 1H), 1.70 (m, 1H) and 1.45 (s, 9H).

IR: (CHCl₃) 1769, 1718, 1506, 1369, 1248, and 1161 cm⁻¹

MS: m/e 482 (M⁺+1)

Analysis Calculated for $C_{25}H_{27}N_3O_5S$:
Calc.: C, 62.35; H, 5.65; N, 8.73;
Found: C, 64.23; H, 5.81; N, 8.93.

Examples 10–18

According to the general methodology of Example 9 and the preceding Examples, the following compounds were prepared.

10. Allyl 7β-t-butoxycarbonylamino-1-carba-(1-dethia)-3-[2-(5-nitrothiazol-2-yl)thiazol-4-yl]-3-cephem-4-carboxylate ¹H NMR: (300 MHz, CDCl₃) δ8.55 (s, 1H), 7.43 (s, 1H), 5.85 (m, 1H), 5.25 (m, 3H), 5.10 (m, 1H), 4.75 (ABX, 2H), 4.95 (m, 1H), 2.98 (dd, J=4, 18Hz, 1H), 2.55 (m, 1H), 2.23 (m, 1H), 1.70 (m, 1H) and 1.45 (s, 9H)

IR: (CHCl₃) 2976, 1772, 1719, 1390, 1351, 1251, and 1159 cm⁻¹

MS: m/e 534 (M⁺+1)

Analysis Calculated for $C_{22}H_{23}N_5O_7S_2$:
Calc.: C, 49.52; H, 4.35; N, 13.13;
Found: C, 50.90; H, 4.33; N, 13.23.

11. Allyl 7β-t-butoxycarbonylamino-1-carba-(1-dethia)-3-[2-(4-fluorophenyl)thiazol-4-yl]-3-cephem-4-carboxylate ¹H NMR: (300 MHz, CDCl₃) δ7.90 (m, 2H), 7.19 (s, 1H), 7.12 (m, 2H), 5.8 (m, 1H), 5.15 (m, 4H), 4.70 (ABX, 2H), 3.90 (m, 1H), 2.95 (dd J=4, 18Hz, 1H), 2.50 (m, 1H), 2.20 (m, 1H), 1.70 (m, 1H), and 1.45 (s, 9H)

IR: (KBr) 3019, 2977, 1770, 1719, 1393, 1336, and 1157 cm⁻¹

MS: m/e 499 (M+)

Analysis Calculated for $C_{25}H_{26}N_3O_5SF$:
Calc.: C, 60.10; H, 5.25; N, 8.41;
Found: C, 62.52; H, 5.57; N, 8.42.

12. Allyl 7β-t-butoxycarbonylamino-1-carba-(1-dethia)-3-[2-(4-pyridyl)thiazol-4-yl]-3-cephem-4-carboxylate ¹H NMR (300 MHz, CDCl₃) δ8.72 ((d, J=9Hz, 2H), 7.75 (d, J=9Hz, 2H), 7.30 (s, 1H), 5.80 (m, 1H), 5.20 (m, 4H), 4.70 (ABX, 2H), 3.95 (m, 1H), 3.0 (dd J=4, 8Hz, 1H), 2.58 (m, 1H), 2.25 (m, 1H), 1.75 (m, 1H), and 1.50 (s, 9H)

IR: (CHCl₃) 3020, 1771, 1718, 1505, 1393, 1348, 1248, and 1161 cm⁻¹

MS: m/e 482 (M+)

Analysis Calculated for $C_{24}H_{26}N_4O_5S$:
Calc.: C, 59.74; H, 5.43; N, 11.61;
Found: C, 58.47; H, 5.23; N, 11.25.

13. Allyl 7β-t-butoxycarbonylamino-1-carba-(1-dethia)-3-[2-(3-methyl-4-nitroimidazol-2-yl)thiazol-4-yl]-3-cephem-4-carboxylate ¹H NMR: (300 MHz, CDCl₃) δ8.10 (s, 1H), 7.40 (s, 1H), 5 62 (m, 1H), 5.25 (m, 3H), 5.08 (d, J=8Hz, 1H), 4.70 (d, J=6Hz, 2H), 4.48 (s, 3H), 3.95 (m, 1H), 3.0 (dd J=4, 18Hz, 1H), 2.58 (m, 1H), 2.25 (m, 1H), 1.75 (m, 1H), and 1.48 (s, 9H)

IR: (CHCl₃) 3018, 1772, 1719, 1530, 1472, 1365, 1270, and 1161 cm⁻¹

MS: m/e 530 (M+)

14. Allyl 7β-t-butoxycarbonylamino-1-carba-(1-dethia)-3-[2-(1,1-(2-pyridyl)(phenyl)methyl)thiazol-4-yl]-3-cephem-4-carboxylate ¹H NMR: (300 MHz, CDCl₃) δ8.60 (d, J=4Hz, 1H) 7.63 (t, J=9Hz, 1H), 7.30 (m, 5H), 7.18 (m, 2H), 7.13 (s, 1H), 7.11 (s, 1H), 5.86 (s, 1H), 5.85 (s, 1H), 5.65 (m, 1H), 5.10 (m, 4H), 4.53 (d, J=6Hz, 1H), 4.47 (d J=6Hz, 1H), 4.28 (dd, J=5, 15Hz, 1H), 4.20 (dd, J=5, 15Hz, 1H), 3.88 (m, 1H), 2.90 (m, 1H), 2.45 (m, 1H), and 1.45 (s, 9H)

IR: (CHCl₃) 3019, 1769, 1718, 1496, 1393, 1369, 1247, and 1160 cm⁻¹

MS: m/e 572 (M+)

Analysis Calculated for $C_{31}H_{32}N_4O_5S$:
Calc : C, 65.02; H, 5.63; N, 9.78;
Found: C, 65.01; H, 5.60; N, 9.52.

15. Allyl 7β-t-butoxycarbonylamino-1-carba-(1-dethia)-3-[2-(p-nitrophenyl)thiazol-4-yl]-3-cephem-4-carboxylate ¹H NMR (300 MHz, CDCl₃) δ8.30 (d, J=9Hz, 2H) 8.05 (d, J=9Hz, 2H) 7.30 (s, 1H), 5.80 (m, 1H), 5.20 (m, 4H), 4.68 (ABX, 2H), 3.95 (m, 1H), 3.0 (dd J=4, 18Hz, 1H), 2.55 (m, 1H), 2.25 (m, 1H), 1.70 (m, 1H), and 1.45 (s, 9H)

IR: (CHCl₃) 3020, 1771, 1719, 1525, 1348, 1248, and 1161 cm⁻¹

MS: m/e 527 (M⁺+1)

Analysis Calculated for $C_{25}H_{26}N_4O_7S$:
Calc.: C, 57.03; H, 4.98; N, 10.64;
Found: C, 57.48; H, 4.82; N, 11.33.

16. Allyl 7β-t-butoxycarbonylamino-1-carba-(1-dethia)-3-[2-(3,4-(t-butyldimethylsilyloxy)phenyl)-thiazol-4-yl]-3-cephem-4-carboxylate ¹H NMR (300 MHz, CDCl₃) δ7.35 (m, 2H), 7.05 (s, 1H), 6.85 (d, J=9Hz, 1H), 5.75 (m, 1H), 5.15 (m, 4H), 4.65 (ABX, 2H), 3.90 (m, 1H), 2.95 (dd J=4, 18Hz, 1H), 2.48 (m, 1H), 2.18 (m, 1H), 1.70 (m, 1H), 1.45 (s, 9H), 1.02 (s, 9H), 1.0 (s, 9H), 0.24 (s, 6H), and 0.21 (s, 6H)

IR: (CHCl₃) 2931, 1768, 1718, 1520, 1472, 1392, 1297, 1254 and 1161 cm⁻¹

MS: m/e 742 (M⁺+1)

Analysis Calculated for $C_{37}H_{55}N_3O_7SSi_2$:
Calc.: C, 59.89; H, 7.47; N, 5.66;
Found: C, 62.22; H, 7.57; N, 5.65.

17. Allyl 7β-t-butoxycarbonylamino-1-carba-(1-dethia)-3-[2-(2-furenyl)thiazol-4-yl]-3-cephem-4-carboxylate ¹H NMR: (300 MHz, CDCl₃) δ7.48 (d, J=2Hz, 1H), 7.10 (s, 1H), 6.95 (m, 1H), 6.5 (m, 1H), 5.80 (m, 1H), 5.15 (m, 4H), 4.68 (ABX, 2H), 3.90 (m, 1H), 2.95 (dd J=4, 18Hz, 1H), 2.50 (m, 1H), 2.20 (m, 1H), 1.70 (m, 1H), and 1.45 (s, 9H)

IR: (CHCl₃) 3019, 1770, 1718, 1502, 1393, 1249, and 1160 cm⁻¹

MS: m/e 472 (M⁺+1)

Analysis Calculated for $C_{23}H_{25}N_3O_6S$:
Calc.: C. 58.59; H, 5.34; N, 8.91;
Found: C, 59.83; H, 5.27; N, 8.41.

18. Allyl 7β-t-butoxycarbonylamino-1-carba-(1-dethia)-3-[2-(3-pyridyl)thiazol-4-yl]-3-cephem-4-carboxylate ¹H NMR: (300 MHz, CDCl₃) δ9.1 (d, J=2Hz, 1H), 8.65 (d, J=4Hz 1H), 8.18 (m, 1H), 7.38 (m, 1H), 7.22 (s, 1H), 5.80 (m, 1H), 5.2 (m, 4H), 4.70 (ABX, 2H), 3.95 (m, 1H), 3.0 (dd J=4, 18Hz, 1H), 2.52 (m, 1H), 2.20 (m, 1H), 1.70 (m, 1H), and 1.48 (s, 9H)

IR: (CHCl$_3$) 3025, 1771, 1717, 1602, 1246, and 1162 cm$^{-1}$

MS: m/e 482 (M+)

Analysis Calculated for C$_{24}$H$_{26}$N$_4$O$_5$S:
Calc.: C, 59.74; H, 5.43; N, 11.61;
Found: C, 59.90; H, 5.62; N, 11.63.

19. Allyl 7β-t-butoxycarbonylamino-1-carba-(1-dethia)-3-[2-(allyloxycarbonylamino)thiazol-4-yl]-3-cephem-4-carboxylate In a procedure analogous to Example 9 above, the title compound was prepared in 38% yield.

$^1$H NMR: (300 MHz, CDCl$_3$) δ8.70 (s, 1H), 5.90 (m, 2H), 5.30 (m, 6H), 4.72 (d, J=6Hz, 2H), 4.65 (d, J=6Hz, 2H) 4.90 (m, 1H), 3.85 (dd J=4, 18Hz, 1H), 2.38 (m, 1H), 2.10 (m, 1H), and 1.45 (s, 9H)

IR: (CHCl$_3$) 3018, 1769, 1722, 1549, 1237, and 1207 cm$^{-1}$

MS: m/e 501 (M+)

Analysis Calculated for C$_{23}$H$_{28}$N$_4$O$_7$S:
Calc.: C, 54.75; H, 5.59; N, 11.10;
Found: C, 54.93; H, 5.31; N, 11.94.

Coproduced in this reaction was allyl 7β-t-butoxycarbonylamino-1-carba(1-dethia)-3-[2-[(allyloxycarbonyl)-(allyl)]amino]-thiazol-4-yl-3-cephem-4-carboxylate (45%).

$^1$H NMR: (300 MHz, CDCl$_3$) δ6.80 (s, 1H), 5.90 (m, 2H), 5.25 (m, 5H), 5.05 (d, J=8Hz, 1H), 4.78 (d, J=6Hz, 2H), 4.65 (d, J=6Hz, 2H), 3.87 (m, 1H), 2.88 (dd J=4, 18Hz, 1H), 2.40 (m, 1H), 2.15 (m, 1H), 1.65 (m, 1H), and 1.45 (s, 9H)

IR: (CHCl$_3$) 3020, 1768, 1712, 1504, 1393, 1242, and 1157 cm$^{-1}$

MS: m/e 544 (M+)

Analysis Calculated for C$_{26}$H$_{32}$N$_4$O$_7$S:
Calc C, 57.34; H, 5.92; N, 10.29;
Found: C, 57.08; H, 5.86; N, 10.09.

It was subsequently discovered that the use of NaH in 1-molar equivalency as base resulted in the desired mono-allylated product.

Example 20

Allyl 7β-[(2-allyloxycarbonylaminothiazol-4-yl)-Z-methoximinoacetylamino]-1-carba(1-dethia)-3-[2-(4-fluorophenyl)thiazol-4-yl]-3-cephem-4-carboxylate A. Deprotection An 80 mg (0.16 mmol) sample of allyl 7β-t-butoxycarbonylamino-1-carba(1-dethia)-3-[2-(4-fluorophenyl)-thiazol-4-yl-3-cephem-4-carboxylate was dissolved in 1 ml of CH$_2$Cl$_2$ and 1 ml of trifluoroacetic acid. The solution was concentrated in vacuo to provide a foam which was again treated with trifluroracetic acid and concentrated out of acetonitrile. From the resulting foam (CH$_2$Cl$_2$/diethyl ether/hexane) was obtained a tan solid.

B. Acylation

In another container, a 46 mg (0.16 mmol) sample of (2-allyloxycarbonylaminothiazol-4-yl)-Z-methoximino acetic acid was dissolved in a small amount of CH$_2$Cl$_2$ and treated with 28 mg (0.16 mmol) of 2-chloro-4,6-dimethoxytriazene and cooled to 0° C. The reaction mixture was then diluted with an additional 1 ml of CH$_2$Cl$_2$ and treated with 19 μl (0.168 mmol) of N-methylmorpholine and stirred for about 40 min. An additional 19 μl g N-methylmorpholine was added, followed by addition of the product from Part A, above, about 2 ml of CH$_2$Cl$_2$ as wash. After 2 hours, the reaction mixture was concentrated in vacuo and purified by column chromatography (silica gel, 30%–40% ethyl acetate/CH$_2$Cl$_2$) to provide 42 mg of the title compound.

$^1$H NMR: (300 MHz, CDCl$_3$) δ9.38 (s, 1H), 7.90 (m, 2H), 7.20 (s, 1H), 7.12 (m, 2H), 5.85 (m, 3H), 5.25 (m, 4H), 4.70 (m, 4H), 4.10 (m, 1H), 4.05 (s, 3H), 3.05 (dd, J=4, 18Hz, 1H), 2.60 (m, 1H), 2.30 (m, 1H), and 1.95 (m, 1H)

Examples 21–30

The following compounds were prepared in a manner analogous to that used in Example 20.

21. Allyl 7β-(2-allyloxycarbonylaminothiazol-4-yl)-Z-methoximinoacetylamino]-1-carba(1-dethia)-3-[(2-phenyl)thiazol-4-yl]-3-cephem-4-carboxylate $^1$H NMR: (300 MHz, CDCl$_3$) δ9.40 (s, 1H), 7.90 (m, 3H), 7.40 (m, 2H), 7.20 (s, 1H), 7.10 (s, 1H), 5.95 (m, 1H), 5.80 (m, 1H), 5.60 (m, 1H), 5.20 (m, 4H), 4.70 (m, 4H), 4.10 (m, 1H), 4.05 (s, 3H), 3.0 (dd J=4, 18Hz, 1H), 2.60 (m, 1H), 2.30 (m, 1H), and 1.95 (m, 1H)

22. Allyl 7β-[2-(allyloxycarbonylaminothiazol-4-yl)-Z-methoximinoacetylamino]-1-carba(1-dethia)-3-[(pyridyl)thiazol-4-yl]-3-cephem-4-carboxylate $^1$H NMR (300 MHz, CDCl$_3$) δ9.55 (s, 1H), 9.10 (s, 1H), 8.65 (d, J=6Hz, 1H) 8.20 (d, J=9Hz, 1H), 8.05 (s, 1H), 7.38 (m, 1H), 7.30 (s, 1H), 7.10 (s, 1H), 5.95 (m, 1H), 5.80 (m, 1H), 5.75 (m, 1H), 5.25 (m, 4H), 4.70 (m, 4H), 4.10 (m, 1H), 4.05 (s, 3H), 3.0 (dd J=4, 18Hz, 1H), 2.60 (m, 1H), 2.30 (m, 1H), and 1.95 (m, 1H)

23. Allyl 7β-[2-(allyloxycarbonylaminothiazol-4-yl]-Z-methoximinoacetylamino]-1-carba(1-dethia)-3-[(1-methyl-2-pyridyl)thiazol-4-yl]-3-cephem-4-carboxylate iodide A 58 mg sample of the title compound of Example 22 was dissolved in 0.9 ml of N,N-dimethylformamide and treated with 17 μl (0.278 mmol) of methyliodide. Crystallization by addition of diethyl ether/hexane to the reaction mixture provided 56 mg (95% yield) of the title compound.

$^1$H NMR: (300 MHz, CDCl$_3$) δ9.15 (s, 1H), 8.80 (d, J=9Hz, 1H), 8.70 (d, J=6Hz, 1H), 8.10 (m, 1H), 7.70 (s, 1H), 7.60 (d, J=9Hz, 1H), 7.25, (s, 1H), 5.95 (m, 1H), 5.75 (m, 1H), 5.55 (m, 1H), 5.25 (m, 4H), 4.65 (m, 4H), 4.35 (s, 3H), 4.05 (m, 1H), 3.95 (s, 1H), 3.05 (dd J=4, 8Hz, 1H), 2.55 (m, 1H), 2.10 (m, 1H), and 1.85 (m, 1H)

24. Allyl 7β-[2-(allyloxycarbonylaminothiazol-4-yl]-Z-methoximinoacetylamino]-1-carba(1-dethia)-3-[2-[5-nitrothiazol-4-yl]thiazol-4-yl]-3-cephem-4-carboxylate $^1$H NMR: (300 MHz, CDCl$_3$) δ9.30 (s, 1H), 8.55 (s, 1H), 7.80 (s, 1H), 7.45 (s, 1H), 7.15 (s, 1H), 5.90 (m, 2H), 5.70 (m, 1H), 5.30 (m, 4H), 4.70 (m, 4H), 4.10 (m, 1H), 4.05 (s, 3H), 3.0 (dd J=4, 18Hz, 1H), 2.60 (m, 1H), and 1.90 (m, 1H)

(using p-toluenesulfonic acid·H$_2$O in place of trifluoroacetic acid)

25. Allyl 7β-[(2-triphenylmethylaminothiazol-4-yl)-Z-triphenylmethoximinoacetylamino]-1-carba(1-dethia)-3-[2-[4-nitro-3-methylimidazol-2-yl]thiazol-4-yl-3-cephem-4-carboxylate (using p-toluenesulfonic acid·H$_2$O in place of trifluoroacetic acid)

$^1$H NMR: (300 MHz, CDCl$_3$) δ8.05 (s, 1H), 7.25 (m, 30H), 6.62 (s, H), 6.58 (d, J=6Hz, 1H), 6.43 (s, 1H), 5.85 (m, 1H), 5.45 (m, 1H), 5.20 (m, 2H), 4.70 (m, 2H), 4.40 (s, 3H), 4.0 (m, 1H), 2.58 (dd, J=4, 18Hz, 1H), 2.35, (m, 1H), 2.10 (m, 1H), and 1.45 (m, 1H)

26. Allyl 7β-[(2-allyloxycarbonylaminothiazol-4-yl]-Z-methoximinoacetylamino]-1-carba(1-dethia)-3-[2-[(phenyl)(2-pyridyl)methyl]thiazol-4-yl]-3-cephem-4-carboxylate ¹H NMR: (300 MHz, CDCl₃) δ9.60 (s, 1H), 8.60 (d, J=4Hz, 1H), 8.05 (s, 1H), 7.60 (m, 1H), 7.25 (m, 5H), 7.20 (m, 1H), 7.12 (s, 1H), 7.0, (s, 1H), 5.80 (m, 3H), 5.20 (m, 4H), 4.50 (m, 4H), 4.10 (m, 1H), 4.0 (s, 3H), 2.90 (m, 1H), 2.50 (m, 1H), 2.20 (m, 1H), and 1.90 (m, 1H)

27. Allyl 7β-[(2-allyloxycarbonylaminothiazol-4-yl]-Z-methoximinoacetylamino]-1-carba(1-dethia)-3-[2-(4-nitrophenyl)thiazol-4-yl]-3-cephem-4-carboxylate (using p-toluenesulfonic acid·H₂O instead of trifluoroacetic acid)

¹H NMR (300 MHz, CDCl₃) δ9.60 (s, 1H), 8.25 (d, J=8Hz, 2H), 8.18 (s, 1H), 8.05 (d, J=8Hz, 2H), 7.35 (s, 1H), 7.05, (s, 1H), 5.90 (m, 3H), 5.25 (m, 4H), 4.70 (m, 4H), 4.15 (m, 1H), 4.05 (s, 3H), 3.0 (dd, J=4, 18Hz, 1H), 2.60 (m, 1H), 2.30 (m, 1H), and 1.95 (m, 1H)

28. Allyl 7β-[(2-allyloxycarbonylaminothiazol-4-yl]-Z-methoximinoacetylamino]-1-carba(1-dethia)-3-[2-allyloxycarbonylaminothiazol-4-yl]-3-cephem-4-carboxylate ¹H NMR (300 MHz, CDCl₃) δ9.60 (s, 1H), 8.52 (s, 1H), 8.10 (s, 1H), 7.02 (s, 1H), 6.80 (s, 1H), 5.90 (m, 3H), 5.70 (m, 1H), 5.25 (m, 6H), 4.70 (m, 6H), 4.05 (m, 1H), 4.0 (s, 3H), 2.88 (dd, J=4, 18Hz, 1H), 2.43 (m, 1H), 2.20 (m, 1H), and 1.90 (m, 1H)

29. Allyl 7β-[(2-allyloxycarbonylaminothiazol-4-yl]-Z-methoximinoacetylamino]-1-carba(1-dethia)-3-[2-(3,4-(t-butyldimethylsilyl)oxy)phenylthiazol-4-yl]-3-cephem-4-carboxylate ¹H NMR (300 MHz, CDCl₃) δ9.45 (s, 1H), 7.95 (s, 1H), 7.35 (m, 2H), 7.12 (s, 1H), 6.84 (m, 1H), 5.95 (m, 1H), 5.75 (m, 2H), 5.25 (m, 4H), 4.65 (m, 4H), 4.10 (m, 1H), 4.02 (s, 3H), 3.0 (dd, J=4, 18Hz, 1H), 2.55 (m, 1H), 2.25 (m, 1H), 1.90 (m, 1H), 1.0 (s, 9H), 0.97 (s, 9H), 0.23 (s, 6H), and 0.18 (s, 6H)

30. Allyl 7β-[(2-allyloxycarbonylaminothiazol-4-yl)-Z-methoximinoacetylamino]-1-carba(1-dethia)-3-[2-(2-furyl)thiazol-4-yl]-3-cephem-4-carboxylate ¹H NMR: (300 MHz, CDCl₃) δ9.55 (s, 1H), 8.05 (s, 1H), 7.48 (s, 1H), 7.15 (s, 1H), 7.05 (s, 1H), 6.95 (m, 1H), 6.52 (m, 1H), 5.85 (m, 3H), 5.25 (m, 4H), 4.70 (m, 4H), 4.10 (m, 1H), 4.02 (s, 3H), 3.0 (dd, J=4, 18Hz, 1H), 2.55 (m, 1H), 2.25 (m, 1H) and 1.95 (m, 1H)

Example 31

Sodium 7β-[(2-aminothiazol-4-yl)-Z-methoximinoacetylamino]-1-carba(1-dethia)-3-[2-(2-phenyl)-thiazol-4-yl]-3-cephem-4-carboxylate A 27 mg (0.0417 mmol) sample of allyl 7β-[(2-allyloxycarbonylaminothiazol-4-yl)-Z-methoximinoacetylamino]-1-carba(1-dethia)-3-[2-(phenyl)-thiazol-4-yl]-3-cephem-4-carboxylate was dissolved in 1.5 ml of CH₂Cl₂, treated with 0.878 mg (0.0013 mmol) of bis triphenylphosphine Pd(II) dichloride and 6 μl (0.0917 mmol) of tri-n-butyltinhydride and stirred for 10 min. The reaction mixture was then treated with an additional 5.0 μl of tri-n-butyltinhydride. After 10 min., the reaction mixture was quenched with a solution of 10 μl concentrated HCl in 0.5 ml of CH₃CN. The resulting mixture was treated with 10 ml of diethyl ether and 10 ml hexane and centrifuged (2X). The resulting solid was dried under vacuum to provide 16.0 mg of the free acid of the title compound (93% pure by HPLC) in 73.7% yield.

A 130 mg (0.248 mmol) of the above was suspended in about 7 ml H₂O and 2 ml CH₃CN. A solution of 25 mg (0.297 mmol) of NaHCO₃ in 1.5 ml of H₂O was prepared and added. The resulting solution was sonicated and passed through an HP20SS column eluting with 8% CH₃CN-18% CH₃CN/H₂O. The desired fractions were concentrated and the resulting title compound washed with diethylether/hexane to provide 125 mg (99.8% pure).

¹H NMR: (300 MHz, d₆-DMSO) δ9.2 (d, J=9Hz, 2H), 7.85 (m, 2H), 7.65 (s, 1H), 7.40 (m, 3H), 7.15 (s, 2H), 6.70 (s, 1H), 5.25 (m, 1H), 3.80 (s, 3H), 3.75 (m, 1H), 2.95 (dd, J=4, 18Hz, 1H), 2.35 (m, 1H), 1.90 (m, 1H), and 1.70 (m, 1H).

IR (KBr): 3500–3100, 1733, 1648, 1591, 1557, 1539, 1405 and 1376 cm⁻¹

MS m/e 547 (M⁺+1)

Analysis calculated for $C_{23}H_{19}N_6O_5S_2Na$:
Calc.: C, 50.54; H, 3.50; N, 15.38;
Found: C, 50.33; H, 3.76; N, 15.17.

Examples 32–38

Examples 32–38 were prepared by methodology analogous to that of Example 31.

32. Sodium 7β-[(2-aminothiazol-4-yl)-Z-methoximinoacetylamino]-1-carba(1-dethia)-3-[2-(2-furyl)-thiazol-4-yl]-3-cephem-4-carboxylate ¹H NMR: (300 MHz, d₆-DMSO) δ9.25 (d, J=9Hz, 1H), 7.80 (s, 1H), 7.65 (s, 1H), 7.20 (s, 2H), 6.95 (m, 1H), 6.70 (s, 1H), 6.60 (m, 1H), 5.25 (m, 1H), 3.80 (s, 3H), 3.75 (m, 1H), 3.85, (dd, J=4, 18Hz, 1H), 2.32 (m, 1H), 1.85 (m, 1H) and 1.65 (m, 1H)

IR (KBr) 3500–3200, 1744, 1647, 1595, 1538, 1404, 1383 and 1035 cm⁻¹

MS: m/e 537 (M⁺+1)

Analysis calculated for $C_{21}H_{17}N_6O_6S_2Na$:
Calc.: C, 47.01; H, 3.19; N, 15.66;
Found: C, 41.14; H, 2.95; N, 11.02.
Residue: 12.74%

33. 7β-[(2-Aminothiazol-4-yl)-Z-hydroxyiminoacetylamino]-1-carba(1-dethia)-3-[2-(4-nitro-3-methylimidazol-2-yl)thiazol-4-yl]-3-cephem-4-carboxylic acid ¹H NMR: (300 MHz, d₆-DMSO) 69.15 (d, J=9Hz, 1H), 8.15 (s, 1H), 7.88 (s, 1H), 7.08 (s, 2H), 6.65 (s,1H), 5.40 (m, 1H), 4.30 (s, 3H), 3.80 (m, 1H), 3.90 (dd, J=4, 18Hz, 1H), 2.38 (m, 1H), 1.95 (m, 1H) and 1.75 (m, 1H)

IR (KBr): 3500–3100, 1754, 1617, 1528, 1397, 1365, 1339, 1268 and 1209 cm⁻¹

MS m/e 560 (M⁺+1)

Analysis calculated for $C_{20}H_{17}N_9O_7S_2$:
Calc.: C, 42.93; H, 3.06; N, 22.53;
Found: C, 42.47; H, 3.38; N, 20.77.

34. 7β-[(2-aminothiazol-4-yl)-Z-methoximinoacetylamino]-1-carba(1-dethia)-3-[2-(1-methyl-3-pyridyl)thiazol-4-yl-3-cephem-4-carboxylic acid ¹H NMR: (300 MHz, D₂O) δ9.30 (s, 1H), 8.90 (d, J=8Hz, 1H), 8.78, (d, J=6Hz, 1H), 8.10 (m, 1H), 7.65 (s, 1H), 6.95 (s, 1H), 5.50, (d, J=6Hz, 1H), 4.45 (s, 3H), 4.10 (m, 1H), 4.0 (s, 3H), 3.95, (m, 1H), 2.58 (m, 1H), 2.20 (m, 1H), and 1.80 (m, 1H)

IR (KBr): 3200, 1758, 1674, 1532, 1384, 1203, and 1168 cm⁻¹

MS: m/e 540 (M⁺+1)

35. Sodium 7β-[(2-aminothiazol-4-yl)-Z-methoximinoacetylamino]-1-carba(1-dethia)-3-[2-(4-nitrophenyl)thiazol-4-yl]-3-cephem-4-carboxylate ¹H NMR: (300 MHz, d₆-DMSO) δ9.25 (d, J=9Hz, 1H), 8.25 (d, J=9Hz, 2H), 8.15 (d, J=9Hz, 2H), 7.85 (s, 1H), 7.15 (s, 2H), 6.72 (s, 1H), 5.25 (m, 1H), 3.80 (s, 3H), 3.75 (m, 1H), 2.95 (dd, J=4, 18Hz, 1H), 2.40 (m, 1H), 1.90 (m, 1H), and 1.70 (m, 1H)

IR (KBr): 3400–3200, 1733, 1649, 1594, 1523, 1402, 1345, 1050 and 851 cm⁻¹

MS: m/e 592 (M⁺+1)

Analysis calculated for $C_{23}H_{18}N_7O_7S_2Na$:
Calc.: C, 46.70; H, 3.07; H, 16.57;
Found: C, 46.06; H, 3.05; N, 15.75.
Residue: 5.84%

36. 7β-[(2-aminothiazol-4-yl)-4-methoximinoacetylamino]-1-carba(1-dethia)-3-[2-(5-nitrothiazol-2-yl)thiazol-4-yl-3-cephem-4-carboxylic acid ¹H NMR: (300 MHz, d₆-DMSO) δ9.35 (d, J=9Hz, 1H), 8.90 (s, 1H), 8.02 (s, 1H), 7.40 (s, 2H), 6.78 (s, 1H), 5.45 (m, 1H), 3.90 (m, 1H), 3.80 (s, 3H), 2.95 (dd, J=4, 18Hz, 1H), 2.40 (m, 1H), 2.0 (m, 1H), and 1.70 (m, 1H)

IR (KBr): 3419, 1764, 1629, 1524, and 1350 cm⁻¹

MS: m/e 532 (M⁺−CO₂)

Analysis calculated for $C_{20}H_{16}N_8O_7S_3$:
Calc.: C, 41.66; H, 2.80; N, 19.43;
Found: C, 41.38; H, 2.90; N, 17.16.

37. 7β-[(2-aminothiazol-4-yl)-Z-methoximinoacetylamino]-1-carba(1-dethia)-3-[2-(4-fluorophenyl)-thiazol-4-yl]-3-cephem-4-carboxylic acid ¹H NMR: (300 MHz, d₆-DMSO) d9.45 (d, J=9Hz, 1H), 7.g5 (m, 2H), 7.65 (s, 1H), 7.35 (m, 2H), 6.83 (s, 1H), 5.50 (m, 1H), 3.95 (m, 1H), 3.90 (s, 3H), 2.95 (m, 1H), 2.40 (m, 1H), 2.0 (m, 1H), and 1.75 (m, 1H)

IR (KBr): 3400–3000, 1762, 1673, 1631, 1517, 1389, 1234, and 1046 cm⁻¹

MS: m/e 543 (M⁺+1)

Analysis calculated for $C_{23}H_{19}N_6O_5S_2F$:
Calc.: C, 50.92; H, 3.53; N, 15.49;
Found: C, 48.53; H, 3.66; N, 13.87.

38. 7β-[(2-aminothiazol-4-yl)-Z-methoximinoacetylamino]-1-carba(1-dethia)-3-[2-(phenyl)(2-pyridyl)methyl)thiazol-4-yl]-3-cephem-4-carboxylic acid ¹H NMR: (300 MHz, d₆-DMSO) 69.28 (d, J=9Hz, 1H), 8.50 (d, J=4Hz, 1H), 7.70 (m, 1H), 7.50 (s, 1H), 7.45 (m, 1H), 7.25 (m, 8H), 6.72 (s, 1H), 5.90 (s, 1H), 5.40 (m, 1H), 3.80 (s, 3H), 2.85 (dd, J=4, 18Hz, 1H), 2.30 (m, 1H), 1.90 (m, 1H), and 1.65 (m, 1H)

IR (KBr): 3400–3000, 1758, 1671, 1619, 1589, 1532, and 1379 cm⁻¹

MS: m/e 616 (M⁺+1)

Analysis calculated for $C_{29}H_{25}N_7O_5S_2$:
Calc.: C, 56.57; H, 4.09; H, 15.93;
Found: C, 55.11; H, 4.09; N, 15.30.

Example 39

Sodium 7β-[(2-aminothiazol-4-yl)-Z-methoximinoacetylamino]-1-carba(1-dethia)-3-(2-aminothiazol-4-yl)-3-cephem-4-carboxylate ¹H NMR (300 MHz, d₆-DMSO) δ9.20 (d, J=9Hz, 1H), 7.15 (s, 2H), 6.70 (s, 1H), 6.60 (s, 2H), 6.55 (s, 1H), 5.20 (m, 1H), 3.78 (s, 3H), 3.62 (s, 1H), 2.64 (dd J=4, 18Hz, 1H), 2.15 (m, 1H), 1.75 (m, 1H) and 1.60 (m, 1H)

IR (KBr) 3500–3100, 1744, 1661, 1607, 1591, 1527, 1382, 1350, and 1034 cm⁻¹

MS m/e 485 (M⁺)

Analysis calculated for $C_{17}H_{16}N_7O_5S_2Na$:

Calc.: C, 42.06; H, 3.32; N, 20.20;
Found: C, 42.38; H, 3.33; N, 18.59.

Example 40

Sodium 7β-[(2-aminothiazol-4-yl)-Z-methoximinoacetylamino]-1-carba(1-dethia)-3-[2-(3,4-dihydroxyphenyl)thiazol-4-yl]-3-cephem-4-carboxylate ¹H NMR: (300 MHz, d₆-DMSO) δ9.50 (s, 1H), 9.25 (d, J=9Hz, 1H), 7.48 (m, 1H), 7.28 (m, 1H), 7.15 (m, 3H), 6.75 (d, J=8Hz, 1H), 6.70 (s, 1H), 5.25 (m, 1H), 3.80 (s, 3H), 3.72 (m, 1H), 2.90, (dd, J=4, 18 Hz, 1H), 2.35 (m, 1H), 1.88 (m, 1H), and 1.65 (m, 1H)

IR (KBr): 3341, 3226, 2223, 1648, 1628, 1600, 1587, 1365, 1253, and 1159 cm⁻¹

MS: m/e 579 (M⁺+1)

Analysis calculated for $C_{23}H_{19}N_6O_7S_2Na$:
Calc.: C, 47.75; H, 3.31; N, 14.55;
Found: C, 42.41; H, 3.24; N, 12.35.
Residue: 7.69%

Example 41

7β-(D-phenylglycylamino)-1-carba(1-dethia)-3-(2-aminothiazol-4-yl)-3-cephem-4-carboxylic acid ¹H NMR: (300 MHz, D₂O) δ7.60 (m, 5H), 6.60 (s, 1H), 5.50 (d, J=4Hz, 1H), 5.22 (s, 1H), 4.0 (m, 1H), 2.70 (dd, J=4, 18Hz, 1H), 2.35 (m, 1H), 1.78 (m, 1H) and 1.35 (m, 1H)

| | IN VITRO ANTIBACTERIAL ACTIVITY* | | | | | | | | | | | | |
|---|---|---|---|---|---|---|---|---|---|---|---|---|---|
| | Staphylococcus | | | | | Streptococcus | | | | H. Influ. | | E. coli | |
| | Aureus | | | | Epi | A | pn | | D | sens | res | | |
| Ex No.*+ | X1.1 | V41 | X400 | S13E | 270 | 222 | C203 | PARK | X66 | 2041 | C.L. | 76 | N10 | EC14 |
| 31 | 1 | 2 | >128 | 128 | 8 | 2 | <.008 | <.008 | >128 | 4 | .06 | .03 | 2 | 1 |
| 32 | 4 | 8 | >128 | 128 | 16 | 4 | .015 | .03 | >128 | 16 | .06 | <.008 | 1 | 1 |
| (retest) 32 | 2 | 4 | >128 | 128 | 8 | 4 | .015 | .03 | >128 | 16 | .03 | .015 | 1 | .5 |
| 33 | .06 | .5 | >128 | 4 | 4 | 1 | <.008 | .015 | 128 | 1 | .06 | .015 | 2 | 1 |
| 34 | 1 | 8 | 128 | >128 | 16 | 4 | .015 | .015 | >128 | 128 | .015 | .015 | .03 | .015 |
| 35 | .5 | 2 | >128 | 32 | 4 | 2 | <.008 | <.008 | >128 | 4 | .03 | .015 | 1 | .5 |
| 36 | .25 | 2 | >128 | 16 | 32 | 1 | 2 | .015 | <.008 | 64 | 4 | .015 | <.008 | .25 | .125 |
| 37 | 1 | 2 | >128 | >128 | 32 | 2 | <.008 | <.008 | >128 | 4 | .03 | .015 | 2 | .5 |
| 38 | 4 | 32 | >128 | >128 | 64 | 64 | <.008 | .015 | >128 | 8 | 2 | .125 | 8 | 4 |
| 39 | 4 | 8 | >128 | >128 | 16 | 32 | <.008 | .015 | >128 | 8 | .06 | .06 | 1 | .5 |
| 40 | 8 | 16 | >128 | 64 | 32 | 16 | .06 | .125 | >128 | 16 | .125 | .015 | .125 | .06 |
| (retest) 40 | 8 | 8 | >128 | 64 | 16 | 16 | .125 | .125 | >128 | 16 | .125 | .03 | .125 | .06 |
| 41 | 4 | 32 | >128 | 64 | 32 | 16 | 2 | 2 | >128 | >128 | 64 | 32 | 128 | 64 |

| | | Enterobacter | | | |
|---|---|---|---|---|---|
| E. coli | Klebsiella | Aerogenes | Cloacea | Salmonella | Pseudomonas |

-continued

IN VITRO ANTIBACTERIAL ACTIVITY*

| Ex No.*+ | TEM | X26 | KAE | X68 | C32 | EB17 | EB5 | 265A | X514 | 1335 | X528 | X239 | PS18 | PS72 |
|---|---|---|---|---|---|---|---|---|---|---|---|---|---|---|
| 31 | 1 | .015 | 1 | 1 | 1 | 1 | 1 | 64 | 2 | 4 | >128 | >128 | >128 | >128 |
| 32 | <.008 | 8 | 1 | 1 | 1 | 1 | 2 | 128 | 1 | 4 | >128 | >128 | >128 | >128 |
| (retest) 32 | .5 | <.008 | 16 | 1 | .5 | 1 | 2 | 128 | 1 | 2 | >128 | >128 | >128 | >128 |
| 33 | 1 | .015 | 2 | 1 | 1 | 1 | 1 | 16 | .5 | 2 | >128 | >128 | >128 | >128 |
| 34 | .125 | <.008 | .25 | .06 | .03 | .03 | .125 | 4 | .015 | .06 | 128 | >128 | 128 | >128 |
| 35 | .5 | <.008 | .5 | 1 | .5 | 1 | 1 | 16 | 1 | 4 | >128 | >128 | >128 | >128 |
| 36 | .25 | <.008 | .5 | .25 | .125 | .25 | 1 | .5 | .25 | .5 | 32 | 32 | >128 | >128 |
| 37 | NG** | <.008 | 2 | .5 | 2 | 1 | 2 | >128 | .5 | 2 | >128 | >128 | >128 | >128 |
| 38 | 4 | .125 | 128 | 4 | 8 | 8 | 8 | >128 | 4 | 8 | >128 | >128 | >128 | >128 |
| 39 | .5 | .015 | 2 | .5 | 1 | .5 | 2 | >128 | 1 | 2 | >128 | >128 | >128 | >128 |
| 40 | .06 | .015 | 8 | .06 | .5 | .03 | .25 | 64 | .03 | .06 | 8 | >128 | 64 | >128 |
| (retest) 40 | .03 | .03 | 4 | .06 | .5 | .06 | .25 | 32 | .03 | .06 | 16 | 128 | 64 | 128 |
| 41 | 64 | 16 | 128 | 128 | 128 | 128 | 128 | >128 | 128 | 128 | >128 | >128 | >128 | >128 |

| | | | Shig. | | Proteus | | | | |
|---|---|---|---|---|---|---|---|---|---|
| | | Serratia | | sonn | morg | incon | rett | Citro | Acin |
| Ex No.*+ | | X99 | SE3 | N9 | PR15 | PR33 | C24 | CF17 | AC12 |
| 31 | | 4 | 8 | 1 | 2 | .5 | .25 | 4 | 128 |
| 32 | | 4 | 16 | 1 | 2 | .5 | .5 | .5 | 128 |
| (retest) 32 | | 2 | 16 | 1 | 2 | .25 | .5 | 1 | 128 |
| 33 | | 2 | 16 | 2 | 4 | .25 | .06 | 4 | 128 |
| 34 | | .06 | .125 | .06 | .06 | .03 | .03 | .015 | 128 |
| 35 | | 4 | 4 | .5 | .5 | .25 | .25 | 2 | 64 |
| 36 | | 1 | 4 | .25 | .25 | .25 | .06 | .06 | 32 |
| 37 | | 4 | 8 | 1 | 2 | .125 | .125 | 4 | 128 |
| 38 | | 8 | 64 | 8 | 32 | 4 | 4 | 32 | 64 |
| 39 | | 1 | 8 | .25 | 4 | .25 | .25 | 8 | 128 |
| 40 | | .25 | 1 | .125 | 4 | .125 | .125 | 4 | 4 |
| (retest) 40 | | .125 | 2 | .125 | 4 | .25 | .25 | 4 | 2 |
| 41 | | 128 | 128 | 128 | 128 | 128 | >128 | >128 | >128 |

*minimum inhibitory concentrations were determined by the Agar-dilution method
+Corresponds to the title compound of the listed Example No.
**"NG" = no growth

We claim:
1. A compound of Formula (2):

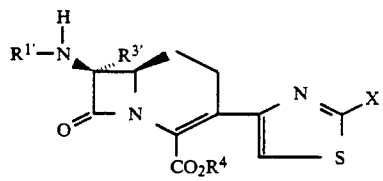

(2)

wherein R¹' is hydrogen or an amino protecting group; R⁴ is hydrogen or a carboxy protecting group; X is selected from the group consisting of amino, halo, cyano, hydrogen, nitro, $C_1$–$C_6$ alkyl, $C_1$–$C_6$ substituted alkyl, a $C_3$ to $C_6$ heterocyclic ring containing 1,2 or 3 nitrogen atoms and 0, or 1 sulfur or oxygen atoms, said ring optionally substituted by one or more groups selected from halo, nitro, hydroxy, $C_1$–$C_6$ alkyl, or $C_1$–$C_6$ substituted alkyl; phenyl, substituted phenyl, or an acyl group of the formula

wherein R''' is $C_1$–$C_6$ alkyl, $C_1$–$C_6$ substituted alkyl, phenyl, or substituted phenyl; and R³' is hydrogen, $C_1$–$C_4$ alkoxy, or a group of the formula —NHCHO.

* * * * *